US010786594B2

(12) United States Patent
Hanson et al.

(10) Patent No.: US 10,786,594 B2
(45) Date of Patent: Sep. 29, 2020

(54) HIGH COHESIVE STRENGTH POLYOLEFIN CONSTRUCTION ADHESIVE

(71) Applicant: H. B. Fuller Company, St. Paul, MN (US)

(72) Inventors: Nolan T. Hanson, Minneapolis, MN (US); Mark S. Kroll, Arden Hills, MN (US)

(73) Assignee: H.B. Fuller Company, St. Paul, MN (US)

(*) Notice: Subject to any disclaimer, the term of this patent is extended or adjusted under 35 U.S.C. 154(b) by 467 days.

(21) Appl. No.: 15/482,331

(22) Filed: Apr. 7, 2017

(65) Prior Publication Data

US 2017/0290945 A1    Oct. 12, 2017

Related U.S. Application Data

(60) Provisional application No. 62/320,139, filed on Apr. 8, 2016, provisional application No. 62/331,122, filed on May 3, 2016.

(51) Int. Cl.

| | | |
|---|---|---|
| *C09J 123/14* | (2006.01) | |
| *C08L 23/14* | (2006.01) | |
| *A61L 15/58* | (2006.01) | |
| *C09J 123/12* | (2006.01) | |
| *C09J 123/00* | (2006.01) | |
| *C09J 123/10* | (2006.01) | |
| *C08L 23/12* | (2006.01) | |
| *C08L 23/10* | (2006.01) | |
| *C08K 5/00* | (2006.01) | |
| *C08L 23/16* | (2006.01) | |
| *A61F 13/515* | (2006.01) | |
| *A61L 15/22* | (2006.01) | |
| *A61L 15/24* | (2006.01) | |
| *C08K 5/01* | (2006.01) | |
| *C09J 123/16* | (2006.01) | |

(52) U.S. Cl.
CPC .......... *A61L 15/585* (2013.01); *A61F 13/515* (2013.01); *A61L 15/225* (2013.01); *A61L 15/24* (2013.01); *C08K 5/0016* (2013.01); *C08K 5/01* (2013.01); *C08L 23/10* (2013.01); *C08L 23/12* (2013.01); *C08L 23/14* (2013.01); *C08L 23/142* (2013.01); *C08L 23/145* (2013.01); *C08L 23/147* (2013.01); *C08L 23/16* (2013.01); *C09J 123/00* (2013.01); *C09J 123/10* (2013.01); *C09J 123/12* (2013.01); *C09J 123/14* (2013.01); *C09J 123/16* (2013.01); *C08L 2205/02* (2013.01); *C09J 2205/102* (2013.01); *C09J 2205/114* (2013.01)

(58) Field of Classification Search
CPC .......... C08L 23/10; C08L 23/12; C08L 23/14; C08L 23/142; C08L 23/145; C08L 23/147; C08L 23/16; C09J 123/00; C09J 123/10; C09J 123/12; C09J 123/14; C09J 123/16

See application file for complete search history.

(56) References Cited

U.S. PATENT DOCUMENTS

| | | | |
|---|---|---|---|
| 6,329,468 B1 | 12/2001 | Wang | |
| 6,627,723 B2 | 9/2003 | Karandinos et al. | |
| 6,653,385 B2 | 11/2003 | Wang et al. | |
| 7,067,585 B2 | 6/2006 | Wang et al. | |
| 7,067,603 B1 | 6/2006 | Karandinos et al. | |
| 7,262,251 B2 | 8/2007 | Kanderski et al. | |
| 8,623,480 B2 | 1/2014 | Davis | |
| 8,709,191 B2 | 4/2014 | Hughes et al. | |
| 8,921,474 B2 | 12/2014 | Alper et al. | |
| 9,115,299 B2 | 8/2015 | Hu et al. | |
| 2003/0096896 A1* | 5/2003 | Wang ............. | C09J 123/10 524/425 |
| 2004/0122196 A1* | 6/2004 | Pierini .......... | C08F 110/06 526/351 |
| 2005/0054779 A1 | 3/2005 | Zhou | |
| 2005/0054780 A1 | 3/2005 | Zhou et al. | |
| 2007/0142801 A1* | 6/2007 | Zhou ............. | C09J 123/02 604/366 |
| 2010/0305259 A1* | 12/2010 | Rodriguez ....... | C09J 123/10 524/504 |
| 2011/0021102 A1 | 1/2011 | Inoue et al. | |
| 2013/0202902 A1 | 8/2013 | Dejesus et al. | |
| 2014/0235127 A1 | 8/2014 | DeJesus et al. | |
| 2014/0358100 A1 | 12/2014 | Remmers et al. | |
| 2015/0024649 A1 | 1/2015 | Czaplewski | |
| 2015/0299526 A1 | 10/2015 | Gray et al. | |

FOREIGN PATENT DOCUMENTS

| | | |
|---|---|---|
| WO | WO 2013/039261 | 3/2013 |
| WO | WO 2014/014491 | 1/2014 |
| WO | WO 2015/051416 | 4/2015 |

OTHER PUBLICATIONS

Sustic, A., et al.; Journal of the Adhesive and Sealant Council, vol. XX, No. 2, 1991, p. 41-58.*
Sustic, A.; Adhesives Age, Nov. 1992, p. 1-5.*
ExxonMobil; Escorez® Tackifier Resins Product Safety Summary, 2016.*
Malpass, D.B., et al.; ntroduction to Industrial Polypropylene: Properties, Catalysts, Processes; 2012, p. 1-4.*
Maier, C., et al.; Polyproyplene: The Definitive User's Guide and Databook, 1998, p. 268-269.*

* cited by examiner

*Primary Examiner* — Robert S Jones
(74) *Attorney, Agent, or Firm* — Kristi Halloran

(57) ABSTRACT

The invention includes a hot melt adhesive composition based on polyolefin polymers that can be used for construction applications in a disposable absorbent article. The olefin based hot melt adhesive composition has surprisingly good cohesive strength and a low odor.

21 Claims, No Drawings

HIGH COHESIVE STRENGTH POLYOLEFIN CONSTRUCTION ADHESIVE

CROSS-REFERENCE TO RELATED APPLICATIONS

This application claims the benefit of two U.S. Provisional Applications having Ser. Nos. of 62/320,139 filed Apr. 8, 2016 and 62/331,122 filed May 3, 2016.

BACKGROUND

Adhesives are often used to bond substrates together so as to maintain the two substrates in a fixed relation to each other. In the area of industrial adhesives, hot melt adhesives are commonly used to bond together a wide variety of articles including disposable absorbent articles comprising non-woven substrates e.g. adult incontinence products, disposable diapers, sanitary napkins, bed pads, puppy pads, medical dressings, etc.

There can be multiple hot melt adhesives used in the manufacture of a disposable absorbent article. For example, in the manufacture of a disposable diaper, hot melt adhesives are used in construction (e.g. bonding the back sheet to the nonwoven and optionally the absorbent pad), elastic attachment (e.g. bonding the elastic material to the back sheet in for example the leg or waist area), and for core stabilization (e.g. applying an adhesive to the absorbent core to increase the strength of the core).

Hot melt adhesives for construction applications formulated with polyolefin polymers tend to have lower cohesive strength than those formulated with styrene block copolymers (SBC). It would be desirable to use polyolefin polymers in hot melt adhesives for construction applications as they tend to have a lower odor. It would be desirable to have a hot melt adhesive for construction applications based on a polyolefin polymer having comparable strength to a hot melt adhesive based on SBC.

SUMMARY

In one aspect, the invention features a hot melt adhesive composition including a first propylene based copolymer that has a co-monomer content of from 5% by weight to 20% by weight and a melt index of no greater than about 20 (190° C., 2.16 kg), a second propylene based copolymer that has a Tg of no greater than −26° C. and a Brookfield Viscosity at 190° C. of no greater than about 20,000 cps, tackifying agent; and plasticizer.

In one embodiment, the tackifying agent is present at no greater than about 42% by weight. In a different embodiment, the tackifying agent is a hydrogenated hydrocarbon.

In another embodiment, the plasticizer is a naphthenic oil. In another embodiment, the plasticizer is present at no less than about 22% by weight. In still another embodiment, the tackifying agent is present at no greater than about 35% by weight and the plasticizer is present at no less than about 25% by weight.

In one embodiment, the hot melt adhesive composition further comprises a wax. In one embodiment, the wax is a polypropylene wax present at from about 2% to about 10% by weight. In another embodiment, the propylene wax has a Mettler softening point of greater than 130° C.

In a different embodiment, the first propylene based copolymer and the second propylene based copolymer are copolymers of propylene and ethylene. In another embodiment, the total amount of propylene-based polymer is present at from about 25% to about 55% by weight.

In one embodiment, the first propylene based copolymer has a co-monomer content of from 7% by weight to about 12% by weight. In another embodiment, the second propylene based copolymer has a viscosity at 190° C. of no greater than about 12,000 cps.

In a different aspect, the invention features a hot melt adhesive composition including from about 6% by weight to about 15% by weight of a first propylene based copolymer that has a co-monomer content of from 5% by weight to 20% by weight and a melt index of no greater than about 20 (190° C., 2.16 kg), from about 15% by weight to about 40% by weight of the second propylene based copolymer having a Tg of no greater than −26° C. and a Brookfield Viscosity at 190° C. of no greater than about 20,000 cps, from about 15% by weight to about 45% by weight of a tackifying agent, from about 20% by weight to about 45% by weight of a plasticizer and from about 2% by weight to about 10% of a polypropylene wax.

In one embodiment, the sum of the first propylene based copolymer, the second propylene based copolymer, the tackifying agent, the plasticizer and the polypropylene wax makes up at least 90% of the hot melt adhesive composition.

In a different embodiment, the hot melt adhesive composition has a Brookfield Viscosity at 300° F. of no greater than 16,000 cps.

In another aspect, the invention features a disposable absorbent article including a first substrate and a second substrate; and the hot melt adhesive composition applied to at least one of the first or second substrates.

In one embodiment, the disposable absorbent article is selected from the group consisting of diaper, adult incontinence article, and sanitary hygiene article. In a different embodiment, the hot melt adhesive composition is used in the disposable article for an application selected from the group consisting of construction and back sheet lamination.

GLOSSARY

In reference to the invention, these terms have the meanings set forth below:

Propylene-based refers to a polymer that comprises at least about 50% by weight propylene.

DETAILED DESCRIPTION

Applicants have discovered a hot melt adhesive composition based on polyolefin polymers that can be used for construction applications in a disposable absorbent article. The olefin based hot melt adhesive composition has surprisingly good cohesive strength (i.e. comparable to, in some cases even better than a SBC based adhesive) and a low odor.

Hot Melt Adhesive Composition

The adhesive composition is a hot melt adhesive composition. The hot melt adhesive composition can be a pressure sensitive adhesive. The hot melt adhesive composition can have an Initial Gardner Color after manufacturing of less than about 3, or even less than about 2. The hot melt adhesive composition can have low odor.

The viscosity of the hot melt adhesive composition can be no greater than about 20,000 cps at around 150° C., no greater than about 16,000 cps at around 150° C., no greater than about 12,000 cps at around 150° C., no greater than about 10,000 cps at around 150° C., or even between about 2,000 cps and 20,000 cps at around 150° C.

The hot melt adhesive composition has a T-Peel that does not decrease over time. The hot melt adhesive composition can have an initial T-Peel (slot coated at 3 grams per square meter) of at least about 100 grams, at least about 150 grams, at least about 200 grams, from about 100 to about 500 grams, or even from about 200 to about 500 grams.

The hot melt adhesive composition can be free of styrene block copolymer. The sum of the first propylene based copolymer, the second propylene based copolymer, the tackifying agent, the plasticizer and the wax can comprise at least 80% of the composition, at least 90% of the composition, or even at least 95% of the hot melt adhesive composition.

Polymer

The hot melt adhesive composition includes two different propylene-based polymers. The two different propylene-based polymers are copolymers with one or more other monomers (e.g. ethylene, butene, pentene, hexane, octene, etc.). In one embodiment, at least one of the polymers is a propylene ethylene copolymer. The propylene-based polymers can be based entirely on olefins, i.e. do not contain any functional groups. The propylene-based polymers can comprise greater than 75% by weight propylene or even greater than 80% by weight propylene. The propylene-based polymers can have a polydispersity (Mw/Mn) of less than about 5, less than about 3, or even about 2. Useful propylene-based polymers include single-site (e.g. metallocene) catalyzed propylene-based polymers and Amorphous Poly Alpha Olefins (APAO's).

The total propylene-based polymer content of the adhesive can be from about 25% by weight to about 55% by weight, from about 30% by weight to about 50% by weight, or even from about 32% to about 47% by weight.

First Propylene-based Copolymer

The first propylene-based polymer can be a single site catalyzed polymer. In one embodiment, the first propylene-based polymer is a single site catalyzed propylene ethylene copolymer. The first propylene-based copolymer has a co-monomer content of from about 5% by weight to about 20% by weight, from about 6% by weight to about 15% by weight, or even from about 7% to about 12% by weight.

The first propylene-based copolymer has a melt index according to ASTM D1238 (190° C., 2.16 kgs) of no greater than about 20, no greater than about 15, no greater than about 12, from about 1 to about 20, or even from about 2 to about 12.

The first propylene-based copolymer is present in the composition at from 5% to about 20% by weight, from about 6% to about 15% by weight, or even from about 7% to about 12% by weight.

Useful commercially available first polymers include VISTAMAXX 3980 FL, VISTAMAXX 3000 and VISTAMAXX 6202 available from ExxonMobil Chemical (Houston, Tex.).

Second Propylene Based Copolymer

The second propylene-based copolymer is selected from a group consisting of single site catalyzed polymers and APAO polymers. The second propylene-based copolymer has a $T_g$ of no greater than –26° C., no greater than –28° C., or even no greater than –30° C.

The second propylene-based copolymer has a Brookfield Viscosity at 190° C. of no greater than about 25,000 cps, no greater than about 20,000 cps, no greater than about 15,000 cps, no greater than about 12,000 cps, no greater than about 10,000 cps, from about 2,500 cps to about 15,000 cps, or even from about 3,000 cps to about 12,000 cps.

The second polymer can be present in the adhesive composition in an amount of at least about 15% by weight, at least about 20% by weight, at least about 25% by weight, at least about 30% by weight, from about 15% to about 50% by weight, or even from about 15% to about 40% by weight. Useful commercially available second polymers include VISTAMAXX 8380 (single site catalyzed propylene ethylene copolymer) commercially available from ExxonMobil Chemical (Houston, Tex.), REXTAC 2585 (APAO) commercially available from Rextac LLC. (Odessa, Tex.) and AERAFIN 180 (APAO) commercially available from Eastman Chemical Company (Kingsport, Tenn.).

Plasticizer

The hot melt adhesive composition includes a plasticizer. Suitable plasticizers include, e.g., naphthenic oils, paraffinic oils (e.g., cycloparaffin oils), mineral oils, phthalate esters, adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil), derivatives of oils, glycerol esters of fatty acids, polyesters, polyethers, lactic acid derivatives and combinations thereof.

Useful commercially available plasticizers include CALSOL 550 oil from Calumet Specialty Products Partners, LP (Indianapolis, Ind.), KAYDOL OIL from Sonnebom (Tarrytown, N.Y.) PARAPOL polybutene from Exxon Mobil Chemical Company (Houston, Tex.), OPPANOL polyisobutylene from BASF (Ludwigsjhafen, Germany), KRYSTOL 550 mineral oil from Petrochem Carless Limited (Surrey, England) and PURETOL 35 mineral oil from Petro Canada Lubricants Inc. (Mississauga, Ontario).

In one embodiment, the plasticizer is a naphthenic oil. The plasticizer is present in the hot melt adhesive composition at no less than about 20% by weight, no less than about 22% by weight, no less than about 25% by weight, no less than about 30% by weight, from about 20% by weight to about 35% by weight, from about 25% by weight to about 35% by weight, or even from about 27% to about 35% by weight.

Tackifying Agent

The hot melt adhesive composition includes a tackifying agent. The tackifying agent can be at least partially hydrogenated in order to improve the odor of the adhesive. The tackifying agent can be fluid or solid at room temperature. Suitable classes of tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof; low molecular weight polylactic acid; and combinations thereof. Examples of useful natural and modified rosins include gum rosin, wood rosin, tall oil rosin, distilled rosin, hydrogenated rosin, dimerized rosin and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin.

Useful tackifying agents are commercially available under a variety of trade designations including, e.g., the ESCOREZ series of trade designations from Exxon Mobil Chemical Company (Houston, Tex.) including ESCOREZ 2203LC, ESCOREZ 5400 and ESCOREZ 5600, the EAS- TOTAC series of trade designations from Eastman Chemical (Kingsport, Tenn.) including EASTOTAC H-100R and EASTOTAC H-100L, the RESINALL series of trade designations from Resinal Corp (Severn, N.C.) including RESINALL 1095S, the KOLON series of trade designations from Kolon Industries, Inc. (Ulsan, Korea) including SUKOREZ SU100 and SU110, the ARKON series of trade designations from Arakawa Chemical Industries, Ltd. (Osaka, Japan) including ARKON M90, ARKON M100 and ARKON P100, the WINGTACK series of trade designations from Cray Valley HSC (Exton, Pa.) including WINGTACK 86, WINGTACK EXTRA, and WINGTACK 95, the PICCOTAC and KRISTALEX series of trade designations from Eastman Chemical Company (Kingsport, Tenn.) including, e.g., PICCOTAC 8095 and. KRISTALEX 3100.

The tackifying agent can be limited in the adhesive to improve heat stability and lower odor. The adhesive composition can include no greater than about 42% by weight, no greater than about 35% by weight, no greater than about 30% by weight, no greater than about 28% by weight, from about 15% by weight to about 45% by weight, from about 20% by weight to about 42% by weight, or even from about 22% by weight to about 32% by weight of a tackifying agent.

Wax

The hot melt adhesive composition can be free of a wax, alternatively the hot melt adhesive composition can include a wax. Useful classes of wax include, e.g., paraffin waxes, microcrystalline waxes, high density low molecular weight polyethylene waxes, by-product polyethylene waxes, polypropylene waxes, Fischer-Tropsch waxes, oxidized Fischer-Tropsch waxes, functionalized waxes such as acid, anhydride, and hydroxyl modified waxes, animal waxes, vegetable waxes (e.g. soy wax) and combinations thereof. Useful waxes are solid at room temperature and preferably have a Ring and Ball softening point of from 50° C. to 70° C. The wax can be a propylene based wax with a Mettler Softening Point (ASTM D 6092) of greater than 130° C., greater than 140° C., or even greater than 150° C. Useful waxes are commercially available from a variety of suppliers including EPOLENE N and C series of trade designations from Westlake Chemical Corporation (Houston, Tex.) including e.g. EPOLENE N-21, EPOLENE N-15 and the LICOCENE series of trade designations from Clariant International Ltd. (Muttenz, Switzerland) including e.g. LICOCENE PP 6102, LICOCENE PP 6502 TP and LICOCENE PP 7502 TP.

The hot melt adhesive composition can include no greater than 10% by weight, no greater than about 5% by weight, from about 2% by weight to about 10% by weight, or even from about 3% to about 8% by weight wax.

Additional Components

The hot melt adhesive composition optionally includes additional components including, e.g., stabilizers, antioxidants, additional polymers (e.g. styrenic block copolymers, polyethylene copolymers), adhesion promoters, ultraviolet light stabilizers, corrosion inhibitors, colorants (e.g., pigments and dyes), fillers, surfactants, wetness indicators, superabsorbents and combinations thereof.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J.), and ETHYL 702 4,4'-methylene bis(2,6-di-tert-butylphenol). When present, the adhesive composition preferably includes from about 0.1% by weight to about 2% by weight antioxidant.

Disposable Absorbent Article

The hot melt adhesive composition can be applied to (i.e. such that it is in direct contact with) or incorporated in a variety of substrates within the disposable absorbent article including, e.g., films (e.g., polyolefin (e.g., polyethylene and polypropylene) films), release liners, porous substrates, cellulose substrates, sheets (e.g., paper, and fiber sheets), paper products, woven and nonwoven webs, fibers (e.g., synthetic polymer fibers and cellulose fibers), elastics and tape backings.

The hot melt adhesive composition is also useful in a variety of applications and constructions including, e.g., disposable absorbent articles including, e.g., disposable diapers, adult incontinence products, sanitary napkins, medical dressings (e.g., wound care products), bandages, surgical pads, pet training pads (e.g. puppy pads) and meat-packing products, and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue).

The hot melt adhesive composition is useful on substrates made from a variety of fibers including, e.g., natural cellulose fibers such as wood pulp, cotton, silk and wool; synthetic fibers such as nylon, rayon, polyesters, acrylics, polypropylenes, polyethylene, polyvinyl chloride, polyurethane, and glass; recycled fibers, and various combinations thereof.

Various application techniques can be used to apply the hot melt adhesive composition to a substrate including, e.g., slot coating, spraying including, e.g., spiral spraying and random spraying, screen printing, foaming, engraved roller, extrusion and meltblown application techniques.

Methods of Making a Disposable Absorbent Article

The hot melt adhesive composition is low in odor and has good cohesive strength. The adhesive also maintains this strength at a low coat weight. These properties make it useful in the construction of disposable absorbent articles.

The hot melt adhesive composition can be used for construction applications. In a typical construction application in the manufacture of a disposable absorbent article, a body fluid impermeable backsheet is bonded to a nonwoven substrate. The adhesive may also be used to bond at least one additional layer or material selected from the group consisting of absorbents, tissues, elastomeric materials, superabsorbent polymers, and combinations thereof. For example, the adhesive can further be used for back sheet lamination i.e. where the body fluid impermeable backsheet typically a polyolefin film (e.g. polyethylene, polypropylene, ethylene vinyl acetate, ethylene copolymer, etc.) is bonded to a second nonwoven to improve the feel of the disposable article.

The hot melt adhesive can also be used to contain and/or provide strength to the absorbent core of a disposable absorbent article (i.e. as a core stabilization adhesive). The absorbent core can include many different materials including natural cellulose fibers (e.g. wood pulp, fibers, cotton, fluff, etc.) and superabsorbent polymers (e.g.polyacrylates).

The invention will now be described by way of the following non-limiting examples. All parts, ratios, percents and amounts stated in the Examples are by weight unless otherwise specified.

EXAMPLES

Test Procedures

Test procedures used in the examples and throughout the specification, unless stated otherwise, include the following.

Viscosity Test Method

Viscosity is determined in accordance with ASTM D-3236 entitled, "Standard Test Method for Apparent viscosity of Adhesives and Coating Materials," (Oct. 31, 1988), using a Brookfield Thermosel viscometer Model RVDV 2 and a number 27 spindle. The results are reported in centipoise (cps).

Glass Transition Temperature ($T_g$)

The $T_g$ was obtained by Differential Scanning Calorimetry (DSC) using a TA Instruments Thermal Analysis—DSC equipped with a Standard Cell RC. The following method was used. The value reported was the mid-point $T_g$ measured during step 8.
1: Equilibrate at 25.00° C.
2: Ramp 10.00° C/min to −80.00° C.
3: Isothermal for 5.00 min
4: Ramp 10,00° C/min to 170.00° C.
5: Isothermal for 5.00 min
6: Ramp 10.00° C/min to −80.00° C.
7: Isothermal for 5.00 min
8: Ramp 10.00° C/min to 160.00° C.
9: Isothermal for 5.00 min
10: End of method Molten Gardner Color The hot melt adhesive composition is tested (in the molten state) to determine Gardner color by comparing the color of the sample against the Gardner Color Standards as set forth in ASTM D-1544. The comparison is made using a Gardner Delta Comparator equipped with an Illuminator available from Pacific Scientific (Bethesda, Md.).

Ti-Peel Test Sample Preparation

A slot coat applicator and laminator are set to the application temperature indicated in the tables, a nip pressure of 41.4 kilopascal (6 psi), an application weight shown in the tables, and minimal rewind and unwind tensions so as not to stretch film. The continuous slot pattern is 7.6 centimeters (3.0 inches) wide. A 0.025 mm (1 mil) thick white embossed polyethylene film that includes a blend of linear low density polyethylene and low density polyethylene (e.g., DH-284 PE MICROFLEX Embossed Non-Breathable film having an emboss gauge of 0.046 mm (1.8 mils) (ASTM D374), 70 gram F50 impact strength (ASTM D1709), 670% elongation at break in the machine direction (ASTM D882), 920% elongation at break in the cross direction (ASTM D882), 590 grams tensile at 10% elongation in the machine direction (ASTM D882), 550 grams tensile at 10% elongation in the cross direction (ASTM D882), 2500 ultimate tensile in the machine direction (ASTM D882), and 1700 grams ultimate tensile in the cross direction (ASTM D882) available from Clopay Plastic Products Company, Inc., (Cincinnati, Ohio) or equivalent thereof), which has been corona treated on one side thereof to surface energy of 38 dynes per square centimeter (dynes/cm2) (as measured using dynes pens), is passed through the applicator. The specified coat weight and pattern of adhesive is applied to the corona treated side of the polymer film and then the film and adhesive are nipped to a 15 grams/square meter (g/m2) basis weight spunbond polypropylene nonwoven web having a 0.18 mm (7 mil) Thwing-Albert thickness (e.g., UNIPRO 45 nonwoven web from Midwest Filtration Company) to form a laminate.

The speed at which the film passes through the applicator is from 213.4 meters per minute (700 feet per minute (ft/min)) to 274.3 meters per minute (900 ft/min) and the adhesive coat weight is as specified. A sufficient amount of laminate is prepared such that 152.4 centimeters (60 inches) of representative lamination can be collected for testing.

T-Peel Test Method

The T-Peel test is used to measure the bond strength of an adhesive coated between two flexible substrates. T-Peel is determined using ASTM D1876-01 entitled, "Test Method for Determining Peel Resistance of Adhesive (T-Peel Test Method)," with the exception that it is run at 30.5 centimeters per minute (12 inches per minute), instead of 25.4 centimeters per minute (10 inches per minute), over a period of 10 seconds, and 7 replicates are run instead of the 10 specified in ASTM D1876. The samples are run on an INSTRON type test instrument. Unless otherwise specified, the test samples are prepared as described in the Sample Preparation. The average peel value over 10 seconds of peeling is recorded, and the results are reported in grams. The initial T-Peel value is the value measured 24 hours after the laminate is prepared.

TABLE 1

Polymer Properties
NA (Not Available)

| | VISTA-MAXX 6202 | VISTA-MAXX 3000 | VISTA-MAXX 3980FL | VISTA-MAXX 3588FL | LICO-CENE 2602 | VISTA-MAXX 8380 | REXTAC 2585 | AERA FIN 180 |
|---|---|---|---|---|---|---|---|---|
| Polymer Type | PP/PE | PP/PE | PP/PE | PP/PE | NA | PP/PE | PP/PE | PP based |
| Ethylene content (wt. %) | 15 | 11 | 9 | 4 | NA | 12 | NA | NA |
| Density | .863 | .873 | .878 | .889 | .88 | .864 | NA | NA |
| Melt Index 190° C./2.16 kg (g/10 min) | 9.1 | 3.6 | 3.7 | NA | NA | NA | NA | NA |
| Brookfield Viscosity @ 190° C. (cps) | NA | NA | NA | NA | 6,300 (@ 170° C.) | 7,570 | 8,500 | 18,000 |
| $T_g$ ° C. | −24 | 27 | −20 | −13 | −24 | −30 | −33 | −40 |

TABLE 2

| | *FULL-CARE 7400 Comparative 1 | Control 1 | Ex 1 | Ex 2 |
|---|---|---|---|---|
| VISTAMAXX 3980FL | | 11.8 | 11.8 | 11.8 |
| LICOCENE 2602 | | 29 | | |
| REXTAC 2585 | | | 29 | |
| AERAFIN 180 | | | | 29 |
| ALIPHATIC HYDROCARBON TACKIFYING AGENT* | | 26 | 26 | 26 |
| CALSOL 550 | | 31 | 31 | 31 |
| IRGANOX 1076 | | 0.2 | 0.2 | 0.2 |
| COEXTRUSION COATING | | 2 | 2 | 2 |
| Molten Viscosity at 300° F. (148.9° C.) (cps) | | 9012 | 11550 | 16100 |
| Peel Strength (grams) - adhesive applied at 163° C. | | | | |
| 1 gsm slot - Initial | 107 | 56 | 72 | 57 |
| 1 gsm slot - 2 weeks aged | 60 | 36 | 93 | 75 |
| 1 gsm slot - 4 weeks aged | 59 | 34 | 88 | 85 |
| 3 gsm slot - Initial | 462 | 99 | 171 | 144 |
| 3 gsm slot - 2 weeks aged | 328 | 59 | 272 | 246 |
| 3 gsm slot - 4 weeks aged | 290 | 50 | 298 | 282 |

*FULL-CARE 7400 is a styrene block copolymer based construction adhesive commercially available from H. B. Fuller.

TABLE 3

| | Control 2 | Ex 3 | Ex 4 | Ex 5 | Ex 6 | Ex 7 |
|---|---|---|---|---|---|---|
| VISTAMAXX 3980FL | | 9 | 14 | 14 | 11.5 | 14 |
| VISTAMAXX 3588 | 11.8 | | | | | |
| VISTAMAXX 8380 | 29 | 35 | 28.8 | 24.4 | 35 | 20 |
| ALIPHATIC HYDROCARBON TACKIFYING AGENT * | 26 | 20 | 20 | 24.4 | 26.3 | 30 |
| CALSOL 550 | 31 | 33.8 | 35 | 35 | 25 | 33.8 |
| IRGANOX 1076 | 0.2 | 0.2 | 0.2 | 0.2 | 0.2 | 0.2 |
| COEXTRUSION COATING | 2 | 2 | 2 | 2 | 2 | 2 |
| Molten Viscosity at 300° F. (148.9° C.) (cps) | Not tested | 7188 | 13800 | 12750 | 15850 | 12550 |
| Peel Strength (grams) - adhesive applied at 163° C. | | | | | | |
| 1 gsm slot - Initial | 56 | 46 | 69 | 106 | 165 | 113 |
| 1 gsm slot - 2 weeks aged | 36 | 124 | 119 | 118 | 135 | 119 |
| 1 gsm slot - 4 weeks aged | 34 | 137 | 109 | 108 | 129 | 124 |
| 3 gsm slot - Initial | 99 | 134 | 143 | 267 | 482 | 424 |
| 3 gsm slot - 2 weeks aged | 59 | 406 | 393 | 363 | 450 | 357 |
| 3 gsm slot - 4 weeks aged | 50 | 470 | 407 | 396 | 444 | 372 |

TABLE 4

| | Ex 8 | Ex 9 |
|---|---|---|
| VISTAMAXX 3980FL | 10 | 8 |
| VISTAMAXX 8380 | 20 | 20 |
| ALIPHATIC HYDROCARBON TACKIFYING AGENT * | 40 | 40 |
| CALSOL 550 | 24.5 | 26.5 |
| EPOLENE N15 | 5 | 5 |
| IRGANOX 10 | 0.5 | 0.5 |
| Molten Viscosity at 325° F. (163° C.) (cps) | 3740 | 2775 |
| Molten Viscosity at 300° F. (148.9° C.) (cps) | 5775 | 5988 |
| Peel Strength (grams) - adhesive applied at 163° C. | | |
| 1 gsm slot - Initial | 88 | 86 |
| 3 gsm slot - Initial | 294 | 332 |

* The aliphatic hydrocarbon tackifying agent is partially hydrogenated, has an aromatic content of less than about 2% and a softening point of from about 95° C. to about 105° C.

The coextrusion coating contains the following in the stated weight percentages:

ESCOREZ 5415-Exxon Mobil Chemical Company (Houston, Tex.) 34.8%

KRATON 01652-Kraton Performance Polymers Inc. (Houston, Tex.) 25%

SHELL: MICROWAX HMP-Shell Deutschland Oil GmbH 39.6%

IRGANOX 1072 0.6%

Other embodiments are within the claims.

What is claimed is:

1. A hot melt adhesive composition comprising:
   a.) a first propylene based copolymer that has a co-monomer content of from 5% by weight to 20% by weight and a melt index of no greater than about 20 (190° C., 2.16 kg);
   b.) a second propylene based copolymer, consisting of a single site catalyzed propylene based copolymer having a $T_g$ of no greater than −26° C. and a Brookfield Viscosity at 190° C. of no greater than about 20,000 cps;
   c.) tackifying agent; and
   d.) a plasticizer.

2. The hot melt adhesive composition of claim 1 wherein the tackifying agent is present at no greater than about 42% by weight.

3. The hot melt adhesive composition of claim 1 wherein the tackifying agent is an at least partially hydrogenated hydrocarbon resin.

4. The hot melt adhesive composition of claim 1 wherein the plasticizer is a naphthenic oil.

5. The hot melt adhesive composition of claim 1 wherein the tackifying agent is present at no greater than about 35% by weight and the plasticizer is present at no less than about 25% by weight.

6. The hot melt adhesive composition of claim 1 further comprising a wax.

7. The hot melt adhesive composition of claim 6 wherein the wax is a polypropylene wax present at from about 2% to about 10% by weight.

8. The hot melt adhesive composition of claim 7 wherein the propylene wax has a Mettler softening point of greater than 130° C.

9. The hot melt adhesive composition of claim 1 wherein the first propylene based copolymer and the second propylene based copolymer are copolymers of propylene and ethylene.

10. The hot melt adhesive composition of claim 1 wherein the total amount of propylene-based polymer is present at from about 25% to about 55% by weight.

11. The hot melt adhesive composition of claim 1 wherein the second propylene based copolymer has a viscosity at 190° C. of no greater than about 12,000 cps.

12. A hot melt adhesive composition comprising:
 a.) from about 6% by weight to about 15% by weight of a first propylene based copolymer that has a co-monomer content of from 6% by weight to 15% by weight and a melt index of no greater than about 20 (190° C., 2.16 kg);
 b.) from about 15% by weight to about 40% by weight of the second propylene based copolymer, selected from the group consisting of single site catalyzed propylene based copolymers and Amorphous Poly Alpha Olefin propylene based copolymer and having a $T_g$ of no greater than −26° C. and a Brookfield Viscosity at 190° C. of no greater than about 20,000 cps;
 c.) from about 15% by weight to about 45% by weight of a hydrogenated hydrocarbon tackifying agent; and
 d.) from about 20% by weight to about 45% by weight of a plasticizer selected from the group consisting of oil, olefin oligomers, polybutenes, polyisoprenes and polybutadienes.

13. The hot melt adhesive of claim 12, where the sum of a.), b.), c.), and d.) makes up at least 90% of the composition.

14. The hot melt adhesive composition of claim 1 having a Brookfield Viscosity at 300° F. of no greater than 16,000 cps.

15. A disposable absorbent article comprising:
 a.) a first substrate,
 b.) a second substrate, and
 c.) the hot melt adhesive composition of claim 1,
 wherein the hot melt adhesive composition is applied to at least one of the first and second substrate.

16. The disposable absorbent article of claim 15 selected from the group consisting of diaper, adult incontinence article and sanitary hygiene article.

17. The disposable absorbent article of claim 15 wherein the hot melt adhesive composition is used in the disposable absorbent article for an application selected from the group consisting of construction and back sheet lamination.

18. The hot melt adhesive composition of claim 1 wherein the first propylene based copolymer is present at from 5% by weight to 20% by weight and wherein the second propylene based copolymer is present at from 20% by weight to 50% by weight.

19. The hot melt adhesive composition of claim 1 wherein the plasticizer is present at from 20% by weight to 35% by weight.

20. The hot melt adhesive composition of claim 12 wherein the plasticizer is selected from the group consisting of oil and polybutene.

21. The hot melt adhesive composition of claim 1 wherein the first propylene based copolymer has a density of from about 0.863 to about 0.878.

* * * * *